United States Patent
Lee et al.

(10) Patent No.: US 7,297,127 B2
(45) Date of Patent: *Nov. 20, 2007

(54) CERVICAL IMMOBILIZATION DEVICE

(75) Inventors: Freddy T. Lee, Boynton Beach, FL (US); Sanjay H. Parikh, Finksburg, MD (US); Ronald M. Rudy, Jr., Boynton Beach, FL (US); Thomas Murphy, Boynton Beach, FL (US)

(73) Assignee: Ambu Inc., Glen Burnie, MD (US)

( * ) Notice: Subject to any disclaimer, the term of this patent is extended or adjusted under 35 U.S.C. 154(b) by 506 days.

This patent is subject to a terminal disclaimer.

(21) Appl. No.: 10/100,162

(22) Filed: Mar. 19, 2002

(65) Prior Publication Data

US 2002/0156409 A1 Oct. 24, 2002

Related U.S. Application Data

(60) Provisional application No. 60/276,499, filed on Mar. 19, 2001.

(51) Int. Cl.
*A61F 5/00* (2006.01)
(52) U.S. Cl. .................... 602/18; 128/DIG. 23
(58) Field of Classification Search ............ 602/17–18, 602/5; 128/845–846, 869–870, DIG. 23; 5/622, 630, 636–637, 640; 606/240
See application file for complete search history.

(56) References Cited

U.S. PATENT DOCUMENTS

| | | | |
|---|---|---|---|
| 373,363 A | 11/1887 | Hard et al. | |
| 678,417 A | 7/1901 | Muller | |
| 1,473,506 A | 11/1923 | Nessler | |
| 1,910,328 A | 5/1933 | Glennan | |
| 1,930,440 A | 10/1933 | Longfellow | 128/87 |
| 2,102,069 A | 12/1937 | Hanicke | 128/87 |
| 2,362,721 A | 11/1944 | Reynolds | 5/82 |
| 2,389,690 A | 11/1945 | Schreiber | 128/87 |
| 2,587,196 A | 2/1952 | Morecroft | 5/327 |
| 2,692,595 A | 10/1954 | Blair, Jr. | 128/87 |
| 2,735,424 A | 2/1956 | Benjamin | 128/87 |
| 2,801,630 A | 8/1957 | Moore | 128/75 |
| 2,818,063 A | 12/1957 | Smith et al. | 128/87 |
| 3,024,784 A | 3/1962 | Monfardini | 128/75 |
| 3,060,930 A | 10/1962 | Grassl | 128/75 |
| 3,337,883 A | 8/1967 | Allison | 5/338 |
| 3,374,785 A | 3/1968 | Gaylord, Jr. | 128/75 |
| 3,449,776 A | 6/1969 | Brock | 5/82 |
| 3,504,667 A | 4/1970 | McFarlane | 128/75 |
| 3,650,523 A | 3/1972 | Darby, Jr. | 269/328 |

(Continued)

*Primary Examiner*—Fenn C. Mathew
(74) *Attorney, Agent, or Firm*—Levy & Grandinetti

(57) ABSTRACT

A cervical immobilization device is disclosed and includes at least one and, preferably, at least two opposite arms that can be folded between a flat and an upright position to engage and support a patient's head. A reversible actuating device folds the arms to the supporting position, and can lock the arms in the folded supporting position. Alternatively, a locking device for locking the position of the arms in the folded supporting position can be provided. The reversible actuating device can be coupled to the arms for folding the arms to an upright position symmetrically and uniformly. In one embodiment, the reversible actuating device is a flexible member that passes around a guide to a position which can be gripped by the user.

16 Claims, 14 Drawing Sheets

U.S. PATENT DOCUMENTS

| | | | |
|---|---|---|---|
| 3,672,364 A | 6/1972 | Rankin | 128/134 |
| 3,696,810 A | 10/1972 | Gaylord, Jr. | 128/75 |
| 3,732,863 A | 5/1973 | Harrington | 128/84 |
| 3,737,923 A | 6/1973 | Prolo | 5/82 |
| 3,756,226 A | 9/1973 | Calabrese et al. | 128/75 |
| 3,814,942 A | 6/1974 | Darden | 250/456 |
| 3,857,390 A | 12/1974 | Harrison | 128/93 |
| 3,957,262 A | 5/1976 | McReynolds | 269/328 |
| 4,034,748 A | 7/1977 | Winner | 128/87 |
| 4,045,678 A | 8/1977 | Rickard | 250/451 |
| 4,211,218 A | 7/1980 | Kendrick | 128/87 |
| 4,267,830 A | 5/1981 | Vick | 128/87 |
| 4,321,718 A | 3/1982 | Chern | 5/437 |
| 4,571,757 A | 2/1986 | Zolecki | 5/82 |
| 4,589,407 A | 5/1986 | Koledin et al. | 128/87 |
| 4,594,999 A | 6/1986 | Nesbitt | 128/87 |
| 4,712,540 A | 12/1987 | Tucker et al. | 128/76 |
| 4,718,412 A | 1/1988 | Nesbitt | 128/87 |
| 4,771,493 A | 9/1988 | Park | 5/437 |
| 4,776,327 A | 10/1988 | Russell | 128/87 |
| 4,794,656 A | 1/1989 | Henley, Jr. | 5/82 |
| 4,899,736 A | 2/1990 | Nesbitt | 128/87 |
| 4,928,711 A | 5/1990 | Williams | 128/869 |
| 4,964,418 A | 10/1990 | Wilson | 128/857 |
| 5,058,572 A | 10/1991 | Schmid et al. | 128/75 |
| 5,058,575 A | 10/1991 | Anderson | 128/87 |
| 5,067,483 A | 11/1991 | Freed | 128/76 |
| 5,146,641 A | 9/1992 | Zwickey | 5/628 |
| 5,207,716 A | 5/1993 | McReynolds et al. | 128/870 |
| 5,211,185 A | 5/1993 | Garth et al. | 128/870 |
| 5,305,754 A | 4/1994 | Honeywell et al. | 128/869 |
| 5,347,669 A | 9/1994 | Neviaser et al. | 5/655 |
| 5,360,393 A | 11/1994 | Garth et al. | 602/17 |
| 5,383,711 A | 1/1995 | Houghteling | 297/397 |
| 5,441,479 A | 8/1995 | Chitwood | 602/18 |
| 5,524,639 A | 6/1996 | Lanier et al. | 128/845 |
| 5,595,191 A | 1/1997 | Kirk | 128/846 |
| 5,622,529 A | 4/1997 | Calabrese | 602/18 |
| 5,657,766 A | 8/1997 | Durham | 128/870 |
| 5,865,773 A | 2/1999 | Koledin | 602/18 |
| 5,891,069 A | 4/1999 | Moffett | 602/18 |
| 5,944,016 A | 8/1999 | Ferko, III | 128/869 |
| 6,158,813 A | 12/2000 | Karash | 297/391 |
| 6,176,549 B1 | 1/2001 | Karash | 297/391 |
| 6,230,712 B1* | 5/2001 | Køhnke | 128/869 |
| 6,244,270 B1* | 6/2001 | Lutian et al. | 128/869 |
| 6,327,723 B1* | 12/2001 | Knight | 5/628 |
| 6,398,747 B1* | 6/2002 | Rudy et al. | 602/18 |

* cited by examiner

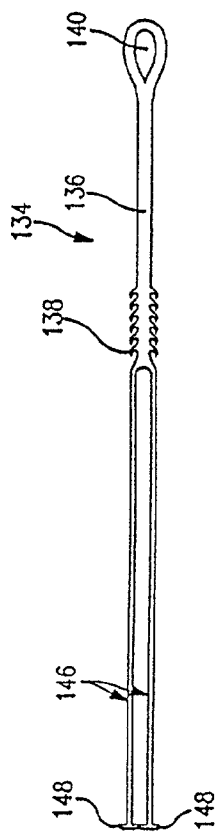
FIG. 11
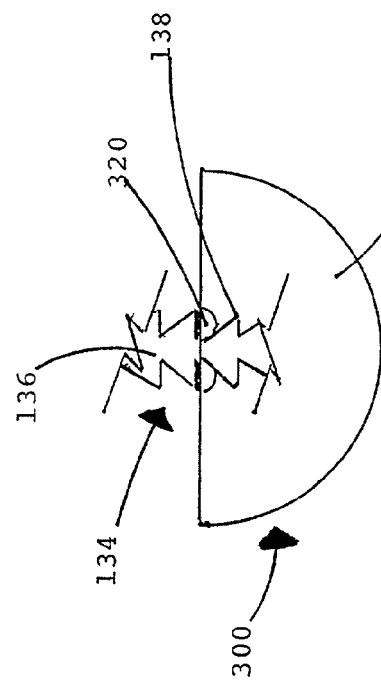
FIG. 14
FIG. 13
FIG. 12

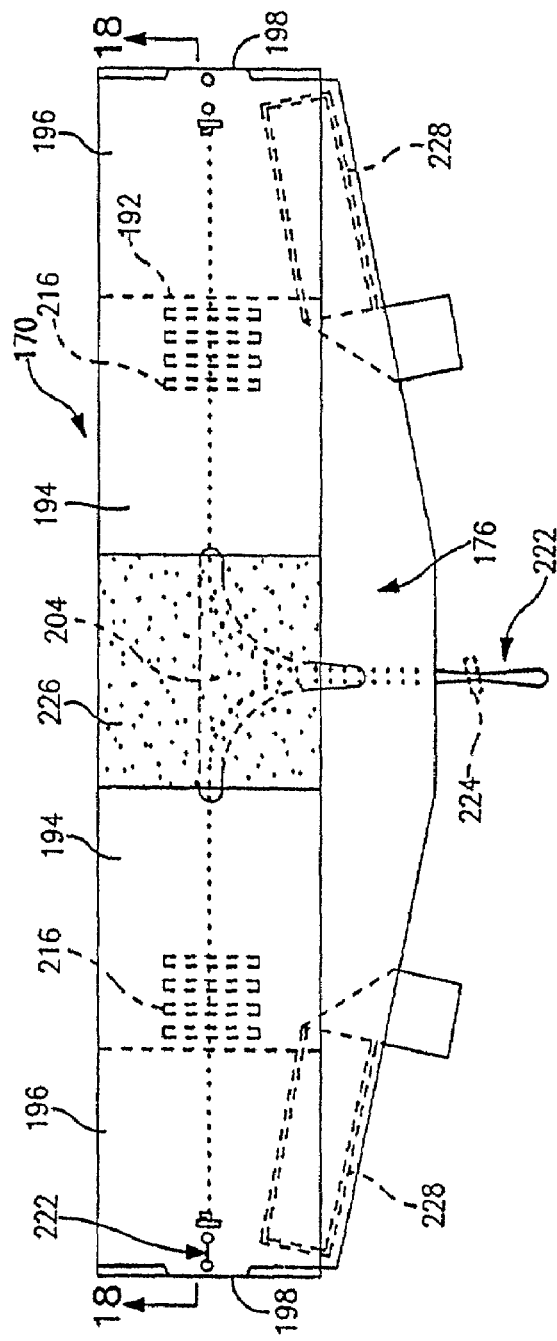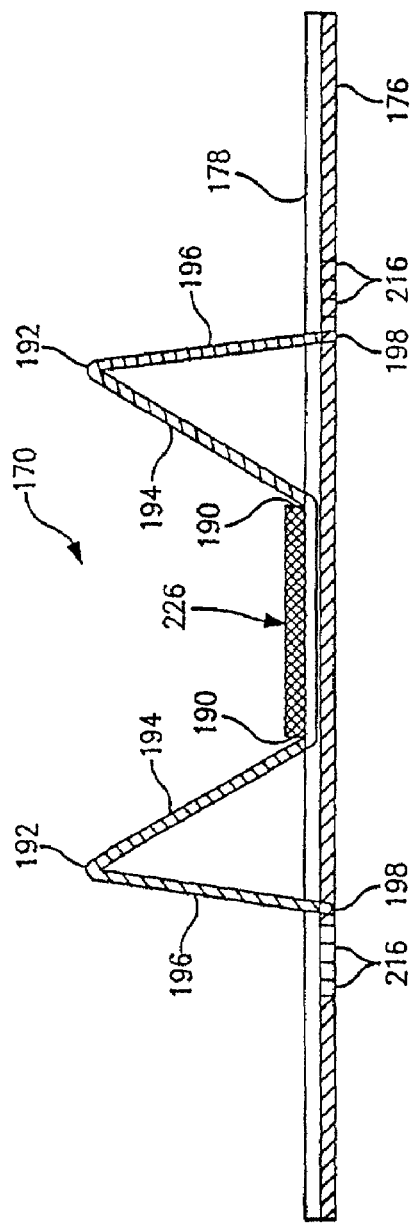

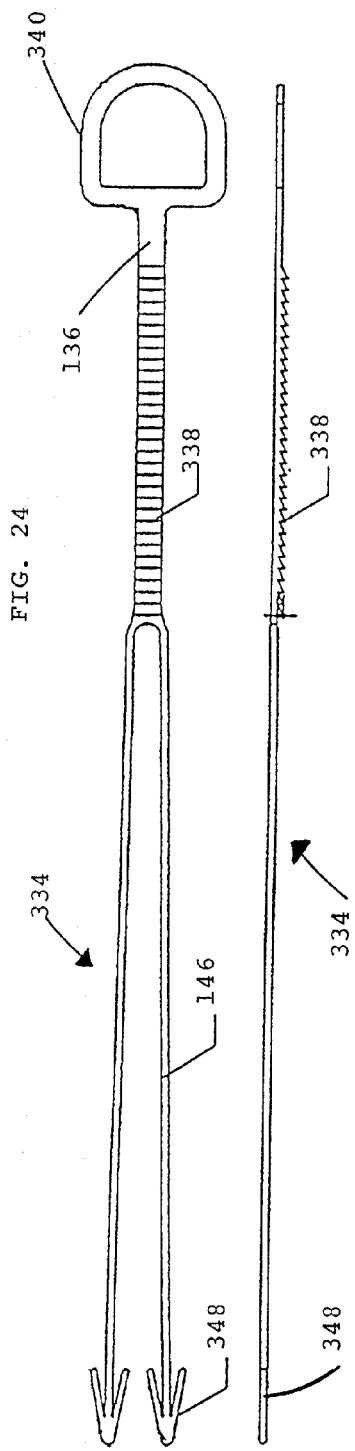
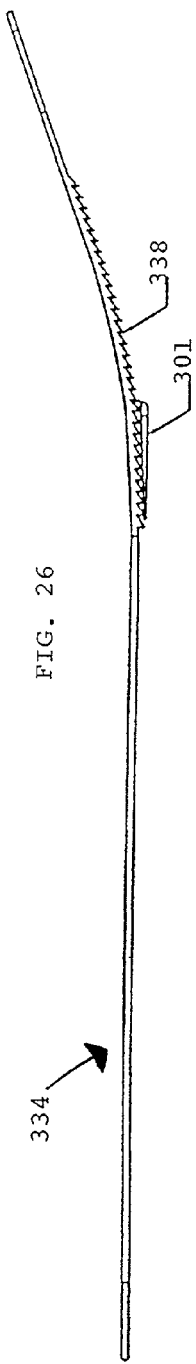
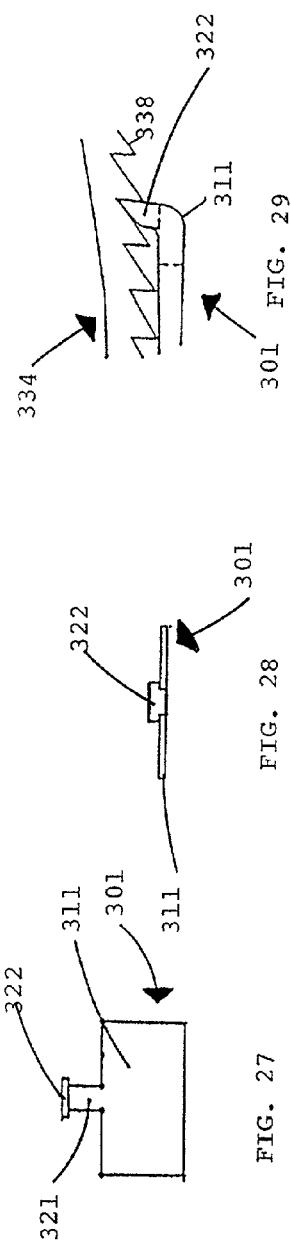
FIG. 24
FIG. 25
FIG. 26
FIG. 27
FIG. 28
FIG. 29

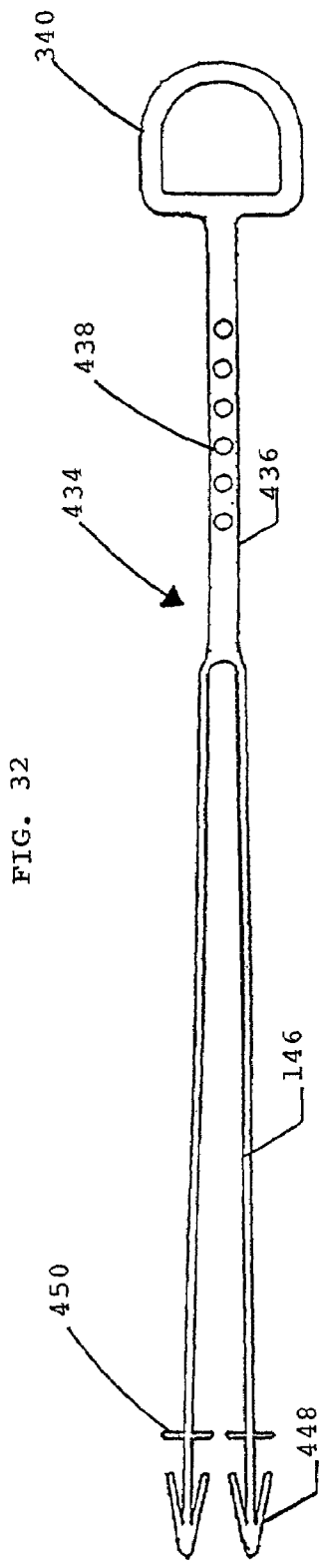
FIG. 32
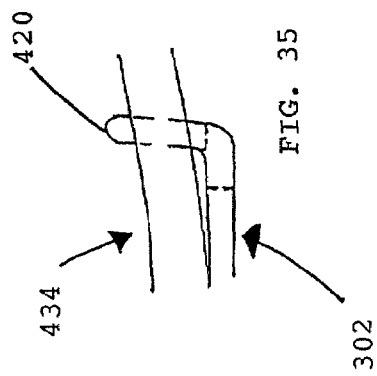
FIG. 35
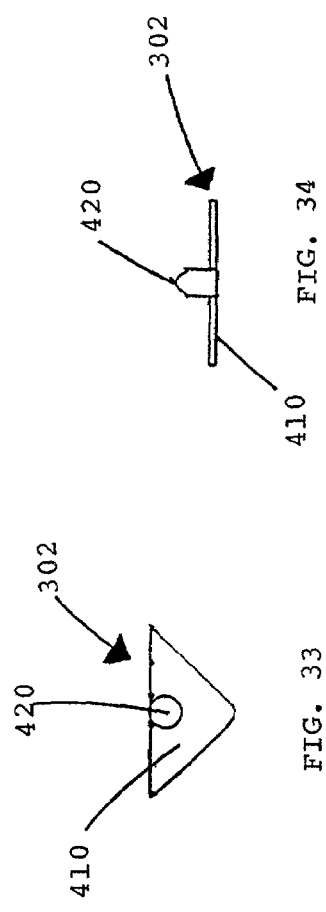
FIG. 34
FIG. 33

CERVICAL IMMOBILIZATION DEVICE

I claim the benefit under Title 35, United States Code, § 120 to U.S. Provisional Application No. 60/276,499 filed Mar. 19, 2001, entitled CERVICAL IMMOBILIZATION DEVICE.

BACKGROUND OF THE INVENTION

1. Field of the Invention

The invention relates generally to a head and cervical immobilization device. More particularly, the invention is a cervical immobilization device that can be erected from a flat condition to an operable condition to minimize movement of the head of an injured patient.

2. Description of the Background Art

It is essential to immobilize the head and cervical portions of patients or accident victims, who have suffered cervical injuries, to prevent further injury during their transport to a medical facility. Several varieties of head and cervical immobilization devices have been used in the emergency medical industry for many years. Some of these devices are designed to fold flat during storage and can be erected when needed.

One type of head immobilization device includes a rigid structural portion that does not require the use of a rigid backboard to transport a patient safely. Examples of this type of device are disclosed generally in U.S. Pat. No. 4,034,748 to Winner, U.S. Pat. No. 4,211,218 to Kendrick, and U.S. Pat. No. 4,594,999 to Nesbit.

Another type of head immobilization device is designed to be attached to a rigid backboard. Examples of this type of device are as follows.

U.S. Pat. No. 4,928,711 to Williams discloses a head immobilizer and method for immobilizing. The device of this patent includes flexible members that are bent independently to wrap around the sides of the head of a patient. The members are secured to a base for locking the position of the members. The head supporting members are attached to the base by a hook and loop fastening means.

U.S. Pat. No. 4,964,418 to Wilson discloses a collapsible cervical immobilization device. This device has a pair of collapsible members with fold lines to enable the members to conform to a patient's head. Rigid support members are then attached to a base by a hook and loop fastening means to restrain the patient's head and neck.

U.S. Pat. No. 5,944,016 to Ferko discloses an adjustable collapsible head immobilizer. This device also has a pair of inner panels that are hinged to a base and conformed to a patient's head. The outer panels have slide tabs that engage a locking mechanism on the base.

The devices of the background art can be effective in immobilizing a patient's head and neck during transport to a medical facility. However, these devices have certain limitations, and there is a continuing need in the industry for improved head immobilization devices. For example, the industry lacks a head immobilization device that can be positioned under a patient's head and smoothly erected and locked into an operable position with minimal manipulation of the device.

SUMMARY OF THE INVENTION

The invention is a cervical immobilization device comprising a base having two opposite ends, a front edge, and a rear edge. The invention includes a cervical immobilizing member coupled to the base. The cervical immobilizing member includes a center portion and at least one movable arm or, desirably, at least two movable arms. Each of the movable arms is foldable between a first position and a second upright or folded position for engaging a patient's head. Each of the movable arms has a pivotal coupling between an inner edge of the arm and the center portion. Each of the movable arms has an outer edge facing outward toward a respective one of the opposite ends of the base. Desirable embodiments of the invention have at least two opposite movable arms for engaging the patient's head when in the second upright position. A reversible actuating device is coupled to each movable arm of the immobilizing member.

The reversible actuating device slides the outer ends of the arms to the second folded position. The reversible actuating device permits at least one of the outer ends of the cervical immobilizing member to slide between the first position toward the center portion and the second upright position for supporting the patient's head. The center portion in desirable embodiments of the invention is a flat panel attached to the base with the arms coupled to the center panel by fold lines. The arms can be moved between the flat or nonoperable first position and the operable second position and back again. The arms can be held in the operable position by friction or by an optional lock. A lock can be permanent, such as certain adhesives, or can be temporary.

BRIEF DESCRIPTION OF THE DRAWINGS

The following is a brief description of the drawings.

FIG. 11 is a top plan view of the reversible actuating device for the cervical immobilization device of FIG. 9.

FIG. 12 is a top plan view of a rigid member or engagement means for the reversible actuating device.

FIG. 13 is a side view of a rigid member or engagement means for the reversible actuating device.

FIG. 14 is a top plan view of a rigid member or engagement means engaging the reversible actuating device.

FIG. 20 is a top plan view of a cervical immobilization device formed from the blank of FIG. 19.

FIG. 21 is a cross-sectional view of the cervical immobilization device of FIG. 20 showing the head supporting arms in the folded position.

FIG. 24 is a top plan view of a reversible actuating device.

FIG. 25 is a side view of a reversible actuating device.

FIG. 26 is a side view of a reversible actuating device engaged by a rigid member or engagement means.

FIG. 27 is a top plan view of a rigid member or engagement means for the reversible actuating device.

FIG. 28 is a rear view of a rigid member or engagement means for the reversible actuating device.

FIG. 29 is a side view of a reversible actuating device engaged by a rigid member or engagement means.

FIG. 32 is a top plan view of a reversible actuating device.

FIG. 33 is a top plan view of a rigid member or engagement means for the reversible actuating device.

FIG. 34 is a rear view of a rigid member or engagement means for the reversible actuating device.

FIG. 35 is a side view of a reversible actuating device engaged by a rigid member or engagement means.

DETAILED DESCRIPTION OF THE INVENTION

Figure 1:
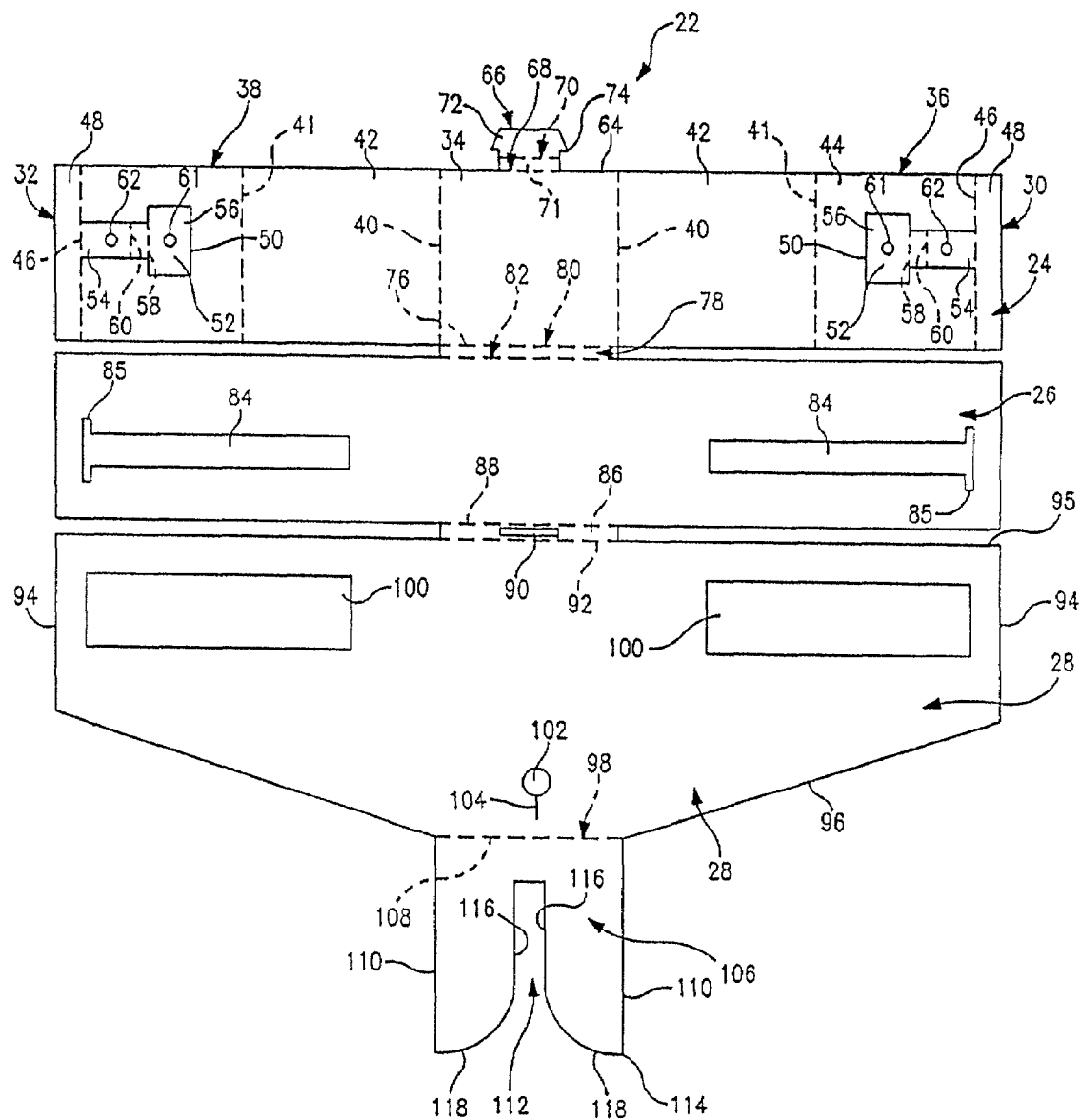
FIG. 1 is a top plan view of a blank for forming the cervical immobilization device in a first embodiment of the invention.

The invention is directed to a cervical immobilization device that can be folded from a generally flat position for storage to a folded upright position for engaging the sides of the head of a patient. The head immobilization device of the invention is suitable for use in combination with a rigid backboard and can be attached to the rigid backboard by an adhesive or other affixing means.

Desirable embodiments of the cervical immobilization device include a separate panel to provide a base. The invention can be made from a single panel wherein at least one head-engaging arm folds and unfolds within a frame. The frame provides a base for affixation to a backboard.

The invention includes a foldable cervical immobilizing member with a reversible actuator or "reversible actuating device." The reversible actuating device is used to fold at least one head-engaging arm. The reversible actuating device permits the head engaging arms to be returned to a flat or storage condition. Desirable embodiments of the reversible actuating device are used to fold and unfold at least one head-engaging arm.

The reversible actuating device can be formed in a variety of shapes and from a variety of materials. Certain embodiments of the reversible actuating device place at least one head-engaging arm in an operable position. Other embodiments of the cervical actuating device place at least one head-engaging arm in an operable position and in a nonoperable position. Either embodiment of the reversible actuating device can be used with a lock. The lock can fix the head-engaging arms permanently or temporarily in one or both positions.

The reversible actuating device can be made from more than one piece. For example the reversible actuating device can include at least two flexible members. Such an embodiment can use a separate flexible member to fold and/or unfold a separate arm or portion of an arm. The multiple pieces can be of the same or different materials.

Embodiments of the reversible actuating device include string and cord. String and cord are flimsy and can be pulled by a user into an operable position to fold at least one arm. The string or cord is reversed or returned to its nonoperable position when a user flattens the arms into a storage position. The flattening of the arms pulls the string or cord back to its nonoperable position.

Other embodiments of the reversible actuating device are made from rigid flat or cord-shaped materials including polymer materials, fibrous materials, leather, and metals. Rigid embodiments of the reversible actuating device can be used to fold and unfold at least one arm. For example, a metal wire can be used as a reversible actuating device such that when the wire is pulled at least one arm is folded, and when the wire is pushed at least one arm is returned to a flat or nonoperable position.

Alternative embodiments of the reversible actuating device can be made of a plurality of parts and/or a plurality of materials. One example is the use of a stiff polymer or metal rod attached to flexible member such as a string or a cord. The rod can be rotated to wind the string or cord and fold the arms. Another example is a rack and pinion combination wherein the parts are made of stiff polymer, metal, or a combination thereof.

The reversible actuating device of the preferred embodiment is desirably used with at least two head-engaging arms and moves these arms between a collapsed, generally flat position and an upright, head-engaging position to support both sides of the patient's head. This embodiment of the reversible actuating device can fold the arms in a substantially symmetrical manner to the upright position to reduce or eliminate twisting of the head and to support each side of the head uniformly. The reversible actuating device is desirably coupled to each of the head-engaging arms so as to fold each of the arms at the same time. This embodiment of the reversible actuating device applies a uniform pressure in opposite directions on each side of the head and prevents twisting of the neck or lateral movement of the head that might occur if the arms were folded one at a time. The reversible actuating device desirably locks the movable arms in the folded position for transport of the patient.

The lock for the arms is optional and can include many embodiments. The lock can be permanent or temporary. The lock can be coupled to the arms in order to prevent their movement in relation to the base. The lock can include as an element or operate with the reversible actuating device. For example, a post and hole mechanism, a ratchet and pawl mechanism, a clamp, a screw mechanism, a button-like device, and/or an equivalent locking means can engage or operate with the reversible actuating device to lock the movement of at least one arm.

The cervical immobilization device can be made from various materials having sufficient strength to support the head of a patient. Desirable embodiments are radiotransparent and can be made from a polymer material of varying grades, strengths, and thicknesses depending upon the intended use. Polymer materials can include sheet plastics, injection molded plastics, and/or thermoformed or rotation molded plastics. Durable polymers are desirable if the device is intended for multiple reuse and sterilization is required between uses. The illustrated and preferred embodiment of the device is made of a suitable cardboard material that is treated with a water repellant coating. A cardboard device has the benefit of being sufficiently inexpensive so as to render the device disposable if it becomes contaminated by body fluids or other matter. Alternative embodiments can be made from combinations of materials including sheet metal, canvass or other fabrics, polymers, and cardboard or other paper products.

The cervical immobilization device is placed under the head of a patient with the center portion positioned directly below the patient's head. The center portion is desirably a panel or a padded material of a dimension to accommodate the head of a patient.

Figure 2:
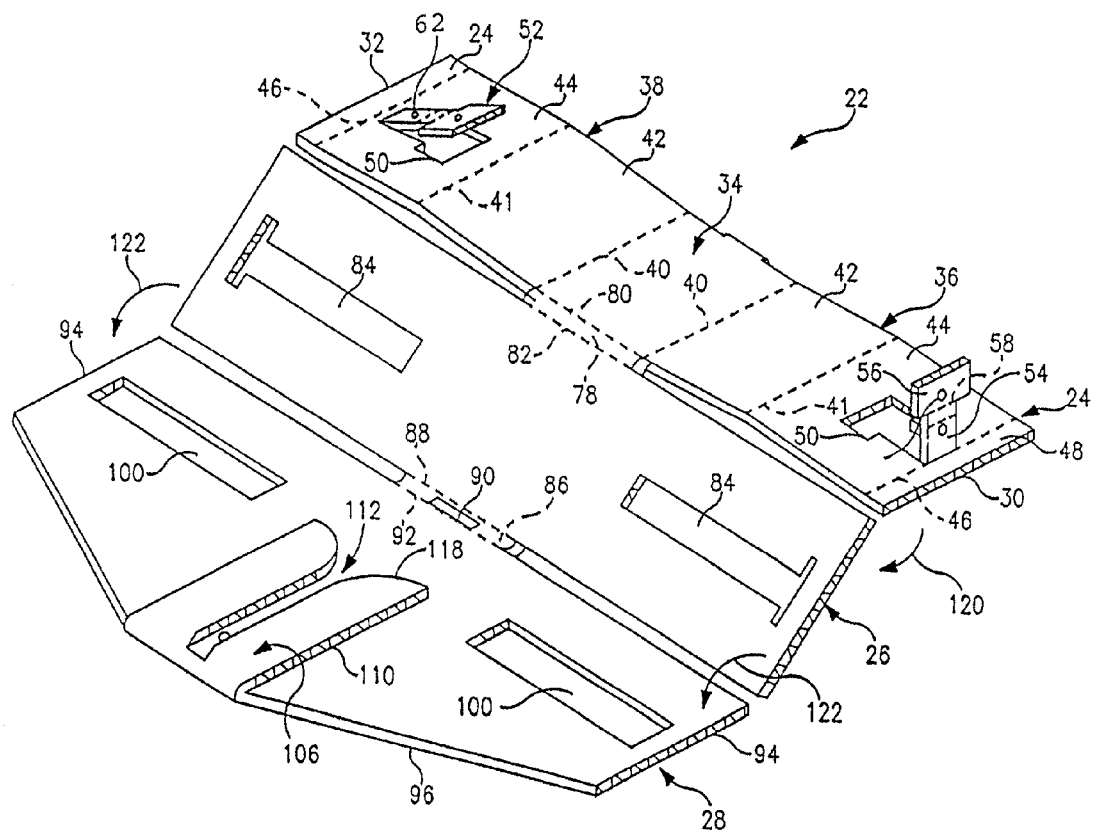
FIG. 2 is a perspective view of the blank of FIG. 1 in a partially folded position.
Figure 3:
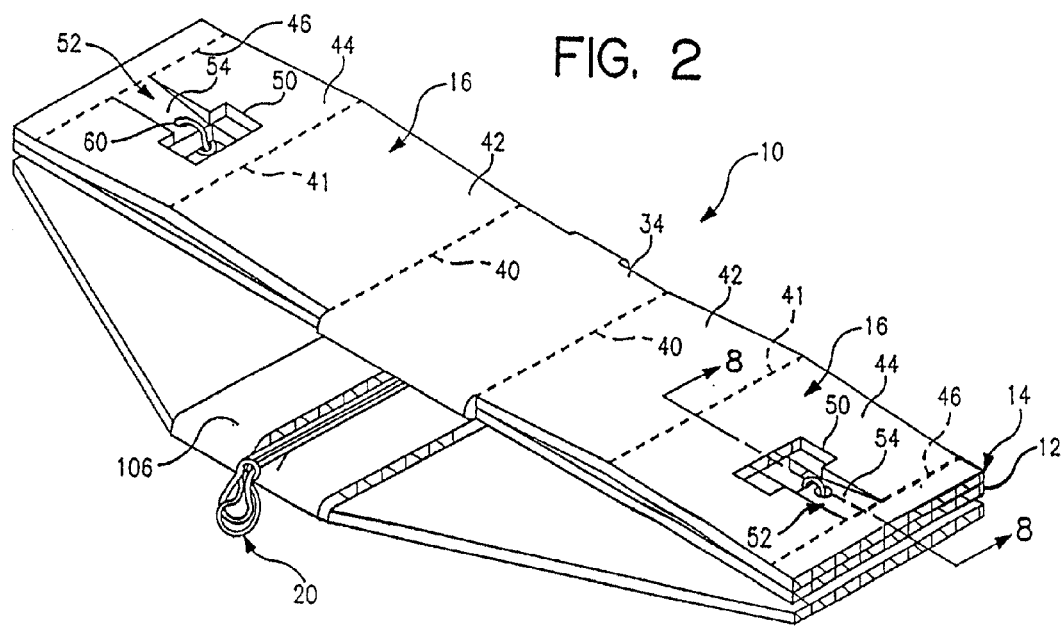
FIG. 3 is a perspective view of the cervical immobilization device formed from the blank of FIG. 1.
Figure 4:
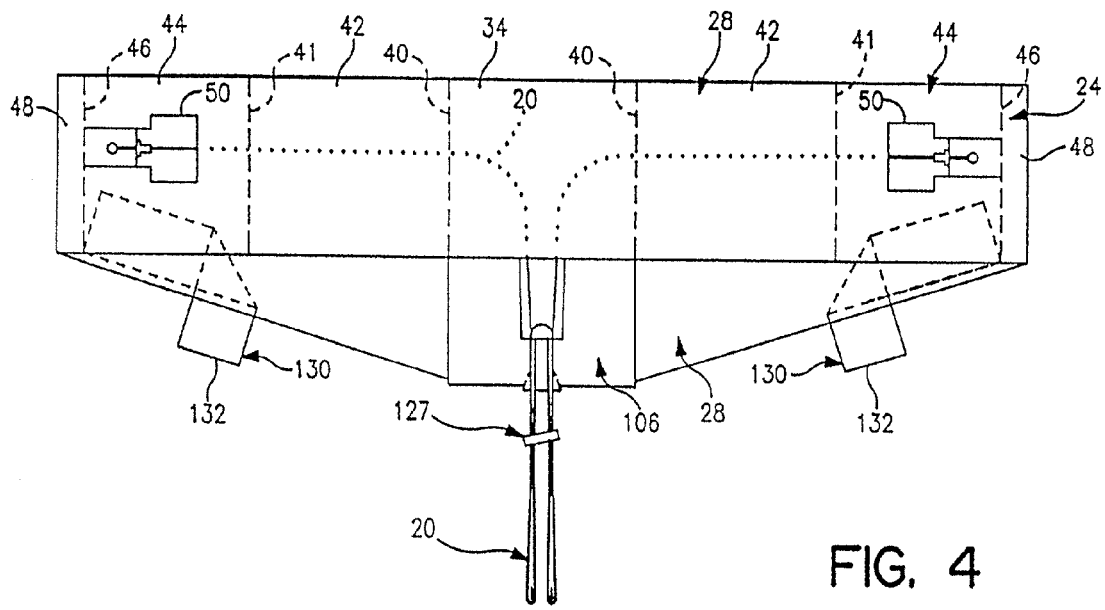
FIG. 4 is a top plan view of the cervical immobilization device formed from the blank of FIG. 1.
Figure 5:
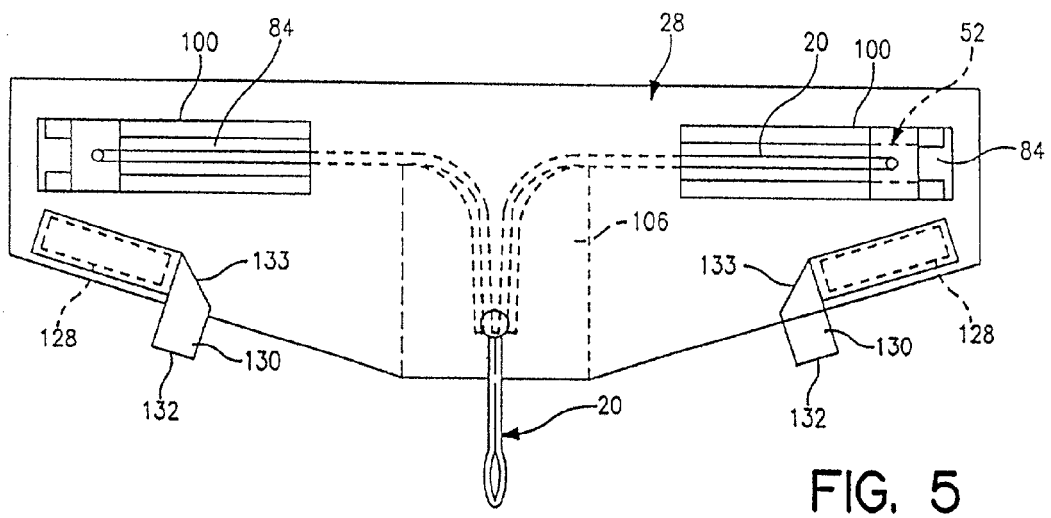
FIG. 5 is a bottom view of the cervical immobilization device formed from the blank of FIG. 1.
Figure 6:
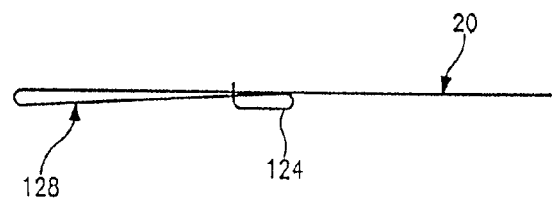
FIG. 6 is a schematic side view of the reversible actuating device and locking arrangement of the cervical immobilization device of the embodiment of FIGS. 1 to 5.
Figure 7:
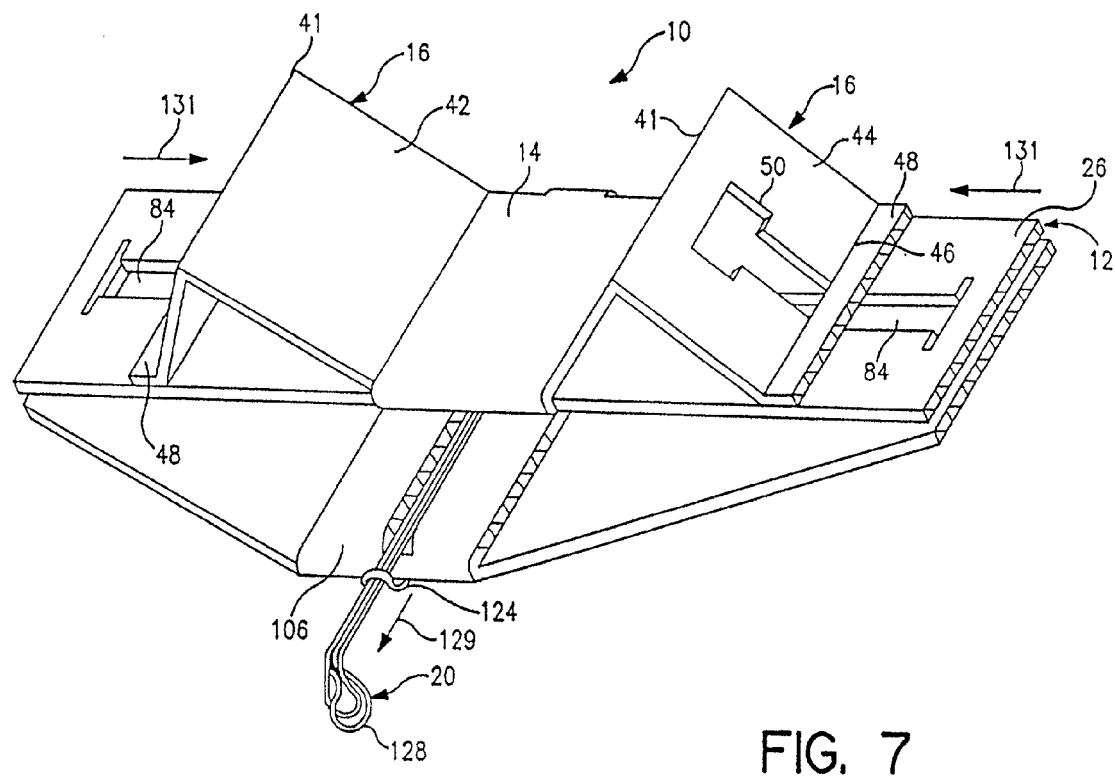
FIG. 7 is a perspective view of the cervical immobilization device in a partially erected position.

FIGS. 1 through 8 illustrate a first embodiment of the assembled cervical immobilization device 10 and blank 22. As shown in FIGS. 3 to 5, the device 10 includes a first base panel 12 and a top panel 14. The top panel 14 includes two opposing arms 16 that can be folded from a flat position as shown in FIG. 3 to a folded upright position as shown in FIG. 7. A reversible actuating device 20 is attached to each of the arms 16 so that the arms 16 can be folded to an upright position substantially simultaneously and symmetrically. Folding the arms 16 symmetrically enables the arms to engage both sides of the patient's head simultaneously to minimize movement of the head and spine during stabilization of an injured patient. In further embodiments, the reversible actuating device is able to move the arms to an upright position one at a time. For this purpose, more than one reversible actuating device can be used.

The cervical immobilization device 10 of the invention is generally made from a suitable sheet material that has sufficient strength to support a patient's head and that can be folded along fold lines or score lines to allow for simple construction. In embodiments of the invention, the head immobilization device is made of corrugated cardboard, although other inexpensive sheet materials such as plastic can be used. In further embodiments, the device can be made from separate components that are coupled together.

The cervical immobilization device 10 is made, in desirable embodiments of the invention, from the unitary cut blank 22 as shown in FIG. 1. In this embodiment of the invention, the blank 22 includes a first panel 24 that forms the top panel 14 of the assembled device 10, a second panel 26 that forms the base 12 of the device 10 and a third panel 28.

The combination of the operable elements provides a "cervical mobilizing member." The cervical immobilizing member in this invention can vary widely and provides at least one operable or "movable" arm with or without center panel. A single fold line, for example, can provide a center portion and a pivotal coupling. The ends and edges of the components can be nonlinear.

The first panel 24 has a substantially rectangular shape with outer ends 30 and 32. The first panel 24 is defined by a center panel 34 and first and second flaps 36 and 38. The first flap 36 is coupled to a side edge of the center panel 34 by a fold line 40. Alternative embodiments can have a single fold line for the center portion or panel but desirably include a pad inserted to receive the patient's head. The first flap 36 includes an intermediate fold line 41 extending parallel to the first fold line 40 to divide the flap 36 into an inner panel 42 and an outer panel 44. Alternative embodiments can use an inner panel of a flexible material, such as canvas or polymer, and an outer panel of a rigid material, such as stiff polymer or metal. A fold line 46 spaced from the end 30 of the first flap 36 forms an end portion 48.

The outer panel 44 includes cut lines 50 to define a tab 52. The tab 52 includes a neck portion 54 coupled to the outer panel 44 along the fold line 46. A head portion 56 is coupled to the neck portion 54 by a fold line 58. A second fold line 60 spaced from the fold line 58 is also provided on the neck portion 54 for folding the head portion with respect to the neck portion 54 as discussed below in greater detail. In desirable embodiments, the head portion 56 has a width greater than the width of the neck portion 54. An aperture 61 is provided in the head portion 56, and an aperture 62 is provided in the neck portion 54 as shown. The second flap 38 is substantially the same as the first flap 36 so that identical elements are shown with the same reference number for simplicity.

The center panel 34 has a first side edge 64 with a coupling tab 66 coupled to the center panel along a fold line 68. A second fold line 70 defines an intermediate portion 71 and a head portion 72. The head portion 72 includes end notches 74 for engaging a slot.

The center panel 34 includes a second edge 76 attached to a coupling panel 78 along a fold line 80. In the embodiment illustrated, the coupling panel 78 has a length substantially equal to the length of the center panel 34. The second panel 26 is coupled to the coupling panel 78 along a fold line 82.

The second panel 26 has a length and width substantially equal to the length and width of the first panel and includes two substantially T-shaped slots 84. Each slot 84 has a longitudinal dimension extending parallel to a longitudinal dimension of the second panel 26. The slot 84 has a width at least equal to the width of the neck portion 54 of the tab 52 and less than the width of the head portion 56. At the outermost end of the slot 84, leg portions 85 defining the T-shape are provided to define a width at least equal to the width of the head portion 56. In a further embodiment, a single slot can be formed having a length to accommodate each of the tabs 52.

A second connecting panel 86 is coupled to the second panel 26 by a fold line 88 and is positioned opposite the coupling panel 78. The connecting panel 86 includes a longitudinal slot 90 dimensioned to receive the coupling tab 66 when the blank 22 is folded to form the cervical immobilization device 10. The third panel 28 is coupled to the connecting panel 86 along a fold line 92.

The third panel 28 has a longitudinal dimension substantially equal to the longitudinal dimension of the first and second panels. Side edges 94 of the third panel 28 extend perpendicular to a rear edge 95 and have a dimension substantially equal to the width of the second panel 26. In the embodiment illustrated, the front edges 96 are angled with respect to the side edges 94 to converge at a leading edge 98. Two longitudinal slots 100 are cut in the third panel 28 and have a length substantially equal to the slots 84. The slots 100 have a width at least as wide as the width of the head 56 of tab 52 so that the head 56 can slide freely along the length of the slot 100. Alternatively, a single slot can be formed to receive the head 56 of each tab 52. An aperture 102 is cut in the third panel 28 proximate the leading edge 98. A slit 104 extends from the aperture 102 toward the leading edge 98.

FIG. 1 illustrates an end panel 106 that is coupled to the leading edge 98 of the third panel 28 along a fold line 108. The end panel 106 has a width substantially equal to the length of the leading edge 98 and parallel sides 110 extending perpendicular to the edge 98. An elongated slot 112 extends from an outer end 114 parallel to the sides 110 and is generally aligned with the aperture 102. The slot 112 includes side edges 116 that are substantially straight and terminate in a curved, convex portion 118.

FIG. 2 illustrates that the cervical immobilization device 10 is assembled by folding the first panel 24 along fold lines 80 and 82 onto the second panel 26 in the direction of arrow 120 and the tab 66 is inserted into the slot 90. The second panel 26 is folded along fold lines 88 and 92 onto the third panel 28 in the direction of arrow 122. The end panel 106 is folded along fold line 108 onto the third panel 28 and secured in place by a suitable adhesive or fastener. The second panel 26 is secured to the end panel 106 by an adhesive. For purposes of illustration, the tabs 52 are shown folded upward from the plane of the first panel 24. During assembly of the cervical immobilization device 10, the tabs 52 are folded downward and inserted through the slots 84 so that the head portion 56 is on the opposite side of the second panel 26 from the first panel 24. The slots 84 and 100 are superimposed so that the head 56 of tab 52 is able to slide.

FIG. 3 illustrates that the assembled cervical immobilization device 10 includes the base 12 formed by the second panel 26 and a top panel 14 formed by the first panel 24. The flaps 36 and 38 of the blank 22 form the folding arms 16. The tab 52 is folded along the fold lines 58 and 60 so that the tab 52 couples the arms 16 to the base 12 in a sliding manner. In this embodiment, the reversible actuating device 20 is a flexible cord or string. Each end of the cord passes through the apertures 61 and 62 of a respective tab 52.

The end panel 106 forms a guide on the third panel 28 for the cord or reversible actuating device 20.

FIGS. 4 and 5 illustrate that the reversible actuating device 20 passes between the arms 16 and the base 12.

Further, the reversible actuating device 20 passes around the convex portions 118 of the end panel 106 and along the open slot 112.

FIG. 6 illustrates the end of the reversible actuating device 20 passing downward through the aperture 102 in the third panel 28 to form a loop 124. The remaining portion of the reversible actuating device 20 that is not passed through the aperture 102 is pulled through the loop 124 to form a second loop 126. A fastener 127 can be attached to the cord to secure the two sections of the cord together.

The cervical immobilization device 10 is desirably used in combination with a rigid backboard (not shown). A double-faced adhesive strip 128 is provided for this use on the bottom face of the third panel 28 along each edge as shown in FIGS. 4 and 5. A release layer 130 having a tab 132 extending outward from the top edge of the device covers the adhesive strip 128. The cervical immobilization device 10 is positioned on a rigid board or other substrate, and the release layer 130 is pulled to separate the release layer from the adhesive strip and expose the adhesive, whereby the device can be attached to the board.

Desirable embodiments of the release layer 130 are of a length that is longer than the length of the adhesive strip 128. The tab 132 can be folded along a fold line 133, generally at about a 45 degree angle, to extend perpendicular to the longitudinal dimension of the adhesive strip. The release sheet is removed by pulling in a direction generally perpendicular to the adhesive strip. Pulling the release sheet peels the release sheet from the adhesive strip.

FIG. 7 illustrates the reversible actuating device 20 when it is pulled in the direction of arrow 129 to apply a tension to the ends of the cord coupled to the tabs 52. Pulling on the reversible actuating device 20 in a desirable embodiment applies a simultaneous and symmetrical force to the tabs 52. This force also pulls the outer ends of the arms 16 inward toward the center panel 32 in the direction of arrows 131. As the outer ends of the arms 16 are drawn toward the center panel 34, the arms 16 fold along the fold lines 40 and 46, whereby the arms 16 assume a folded, upright, substantially inverted V-shaped configuration as shown in FIG. 7. The inner panels 42 preferably, simultaneously contact the opposite sides of the patient's head with substantially uniform pressure and tension to eliminate or reduce movement of the patient's head during the folding of the arms 16.

Alternatively, the reversible actuating device 20 can be arranged to apply a nonuniform force against each side of the patient's head as needed and to move the arms separately from the flat position to the folded upright position. For example, the cord attached to each tab can be pulled separately to raise separately the respective arm to the folded position. In still further embodiments, at least two separate reversible actuating devices can be included to move selectively a respective number of arms to the upright position at a desired time. One such alternative embodiment (not shown) has four arms wherein two arms are used to support each side of the patient's head.

Once the arms 16 are folded to the desired upright position, the position of the arms is locked by pulling on the cord or reversible actuating device 20 to tighten the first loop 124 around the cord and to pull the cord or reversible actuating device 20 into the slit 104. The slit 104 is sufficiently thin to grip the cord or reversible actuating device 20 by friction. The loop arrangement of the cord or reversible actuating device 20 enables the cord to be cinched and held in a fixed position and to provide infinite adjustment of the position of the arms 16 with respect to the base 12. The inner panels 42 are desirably able to bend slightly to conform to the shape of the patient's head as the cord is pulled and supports the user's head by preventing movement and preventing further injury. A plurality of fold lines (not shown) can be provided on the inner panels 42 to allow the inner panels to fold and conform to the patient's head. The patient can be removed from the device 10 by loosening the loop 124, thereby loosening the cord and allowing the arms 16 to be unfolded and moved away from the patient's head. In actual use, an adhesive-backed tape or strap is generally attached to the arms 16 and passed over the forehead of the patient to secure the patient's head to the cervical immobilization device 10.

The cervical immobilization device 10 can be made from a folded blank having a variety of arrangements of panels different from the embodiment of FIG. 1. In further embodiments, the panels can be separate elements that are assembled and secured together by adhesives or other fasteners. Other locking devices can be used to lock the reversible actuating device in a fixed position and retain the arms in the upright position. For example, a post or button-like device can be attached to the upper surface of the cervical immobilization device so that a cord can be wrapped around the post to secure the cord in place. The post or button-like device can be attached to the upper surface of the cervical immobilization device.

Figure 8:
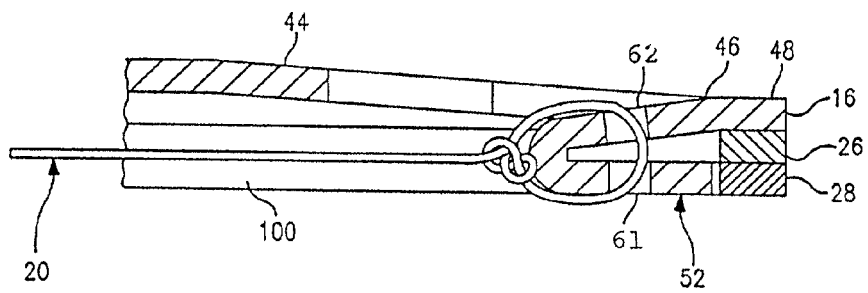
FIG. 8 is a partial cross-sectional view of the reversible actuating device and sliding arrangement for the foldable arms as seen along line 8-8 of FIG. 3.

FIG. 8 is a partial cross-sectional view of the reversible actuating device 20 and sliding arrangement for the foldable arms as seen along line 8-8 of FIG. 3. The reversible actuating device 20 passes through apertures 61 and 62 of tab 52. The reversible actuating device 20 of this embodiment is a cord and is tied into a knot. Desirable embodiments of the reversible actuating device 20 are made from a polymer material, such as plastic, and are fused together or include a prong or hook (not shown) to fix the end of the reversible actuating device 20 in at least one aperture of tab 52. The use of a stiff polymer, flexible metal, or similar material permits the reversible actuating device 20 to push the arm back to a first nonoperable or flat position for storage. The knot or fused loop in these embodiments provides a pushing means.

Figure 9:
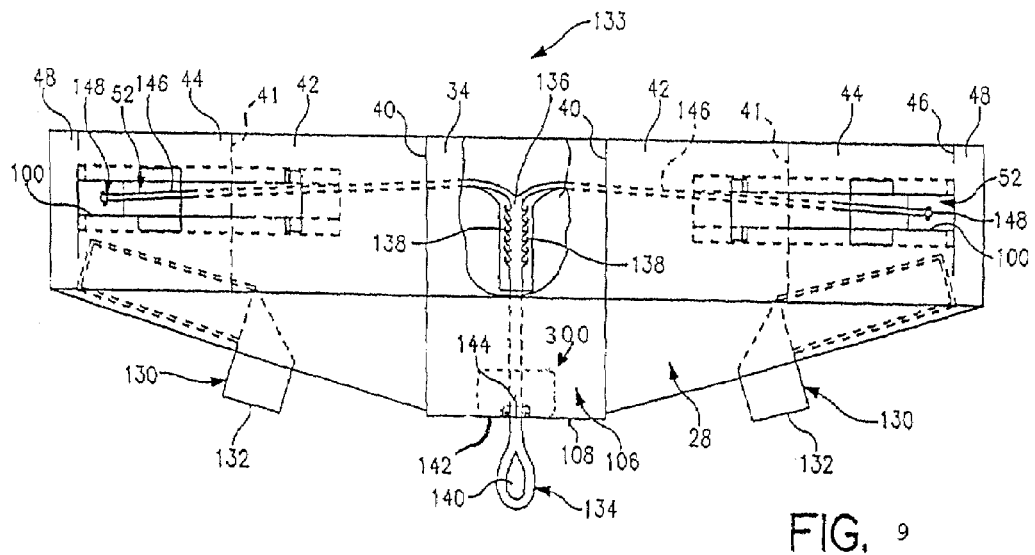
FIG. 9 is a top plan view of the cervical immobilization device in a second embodiment of the invention.
Figure 10:
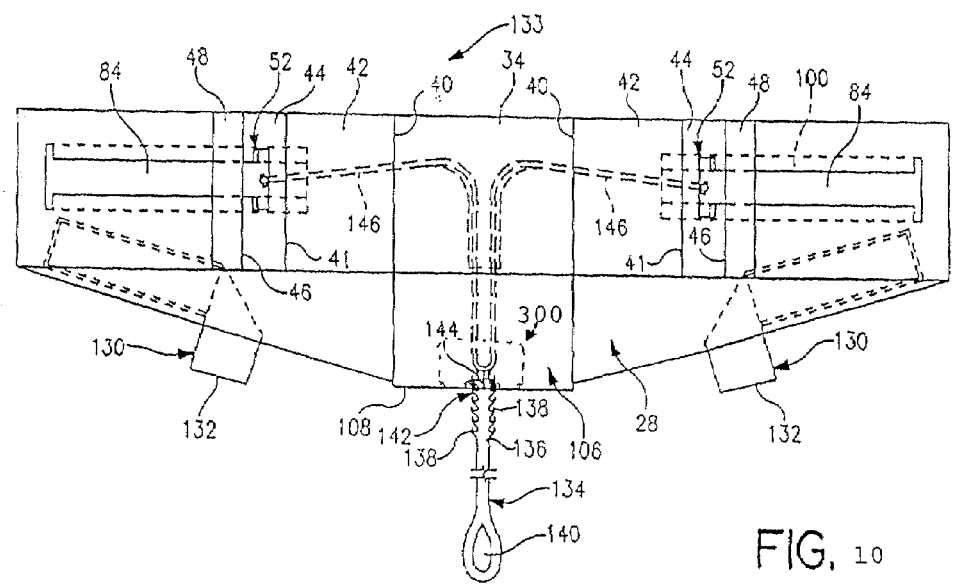
FIG. 10 is a top plan view of the cervical immobilization device of the embodiment of FIG. 9 showing the head supporting arms in the erected position.

FIGS. 9 through 17 illustrate a second embodiment of the cervical immobilizing device 133 of the invention as illustrated in FIGS. 9 through 11 and is similar to the immobilizing device 10 of the embodiment of FIG. 1 except for the reversible actuating device 134. The cervical immobilizing device 133 of this embodiment is made from a blank substantially the same as the blank 22 of FIG. 1. Accordingly, identical components and parts of the cervical immobilizing device 133 are identified by the same reference number. In this embodiment, the reversible actuating device 134 includes a body portion 136 having a plurality of sizing positions or ratcheting teeth 138 on opposite sides of the body portion 136. A gripping end 140 is provided in the form of a loop. In this embodiment, a slit 142 is provided along the fold line 108 having a length substantially equal to the width of the body portion 136 and less than the outer dimension of the teeth 138. A transverse slit 144 is cut perpendicular to the slit 142 to allow the loop 140 to be inserted and positioned in the slit 142. In the embodiment illustrated, the transverse slit 144 is formed in the end panel 106 so that the transverse slit 144 appears on the top portion of the cervical immobilizing device 133. Alternatively, the transverse slit 144 can be formed in the panel 28 to appear on the bottom of the device 133. As shown in the cut-away view of FIG. 9 and the top view of FIG. 8, the reversible actuating device 134 includes at least one but preferably two or more flexible leg members 146 extending from the body portion 136 to the tabs 52. The flexible leg members 146 include an attachment means to engage the cervical immobilizing member. The attachment means in this embodiment is an enlarged T-shaped head 148 for passing through the apertures 61 and 62 and coupling with the tab 52.

FIGS. 9 through 11 illustrate an embodiment of the cervical immobilizing device 133 that is used in a similar manner as the embodiment of FIGS. 1 through 8. The immobilizing device 133 is fixed to a rigid backboard, and the patient's head is placed on the center panel 34 with the reversible actuating device 134 extending away from the patient's body. The loop 140 is pulled away from the immobilizing device 133 so that the flexible legs 146 of the reversible actuating device 134 pull the ends of the arms 16 toward the center panel 34 and fold the arms 16 along the fold lines 40 and 41 to the upright position. The reversible actuating device 134 is pulled until the teeth 138 pass through the slit 142 so that the teeth reversibly engage a rigid member (not shown) of the immobilizing device 133.

The rigid member of the cervical immobilizing device 133 can be the connecting panels 86 and 88 as illustrated in FIG. 1. A provision must exist whereby the reversible actuating device 134 can be lifted, twisted, or otherwise manipulated so as to disengage the teeth 138 from the rigid member and the reversible actuating device 134 can be returned to its inoperable position. The arms 16 can then be pressed back into a flat storage position. Certain embodiments of the cervical immobilizing device 133 can include an attachment, abutment, or similar means (not shown) on the flexible leg members 146 such that return of the reversible actuating device 134 to the inoperable position also flattens the arms 16 into a storage position. A rigid member can be a portion of the immobilizing device 133 as described above or a separate element.

FIGS. 12 and 13 illustrate an embodiment of a rigid member 300. The rigid member 300 has a flat base 310 of any geometrical shape that supports at least one engagement means or in this embodiment a prong 320. The prong 320 can be any geometrical shape which engages the teeth 138 of the reversible actuating device 134. The rigid member 300 is sandwiched between the third panel 28 and the end panel 106 such that the prongs 320 project from the slit 142 as shown in FIGS. 9 and 10.

FIG. 14 illustrates an enlargement of the rigid member 300 engaging the reversible actuating device 134. The embodiment of the rigid member 300 of this figure has straight-edged teeth 138, which engage two prongs 320. The two prongs 320 have a complementary flat face to engage the flat edge of the teeth 138.

In operation, the reversible actuating device 134 is pulled from the immobilizing device 133 over the top of the prongs 320 until the arms 16 securely engage the head of a patient. Upon securely engaging the head of a patient, the reversible actuating device 134 is pressed between the two prongs 320 to fix the patient's head. The arms 16 of the immobilizing device 133 are returned to their inoperable position by lifting the reversible actuating device 134 from the prongs 320 and pushing the reversible actuating device 134 back into the immobilization device 133. The return of the reversible actuating device 134 to its inoperable position permits the arms 16 to be pressed into their flat position.

FIGS. 15 to 18 illustrate another embodiment of the invention. The cervical immobilization device 150 in this embodiment is similar to the device of FIG. 1. For this reason, similar elements for this embodiment are identified by the same reference numbers.

Figure 15:
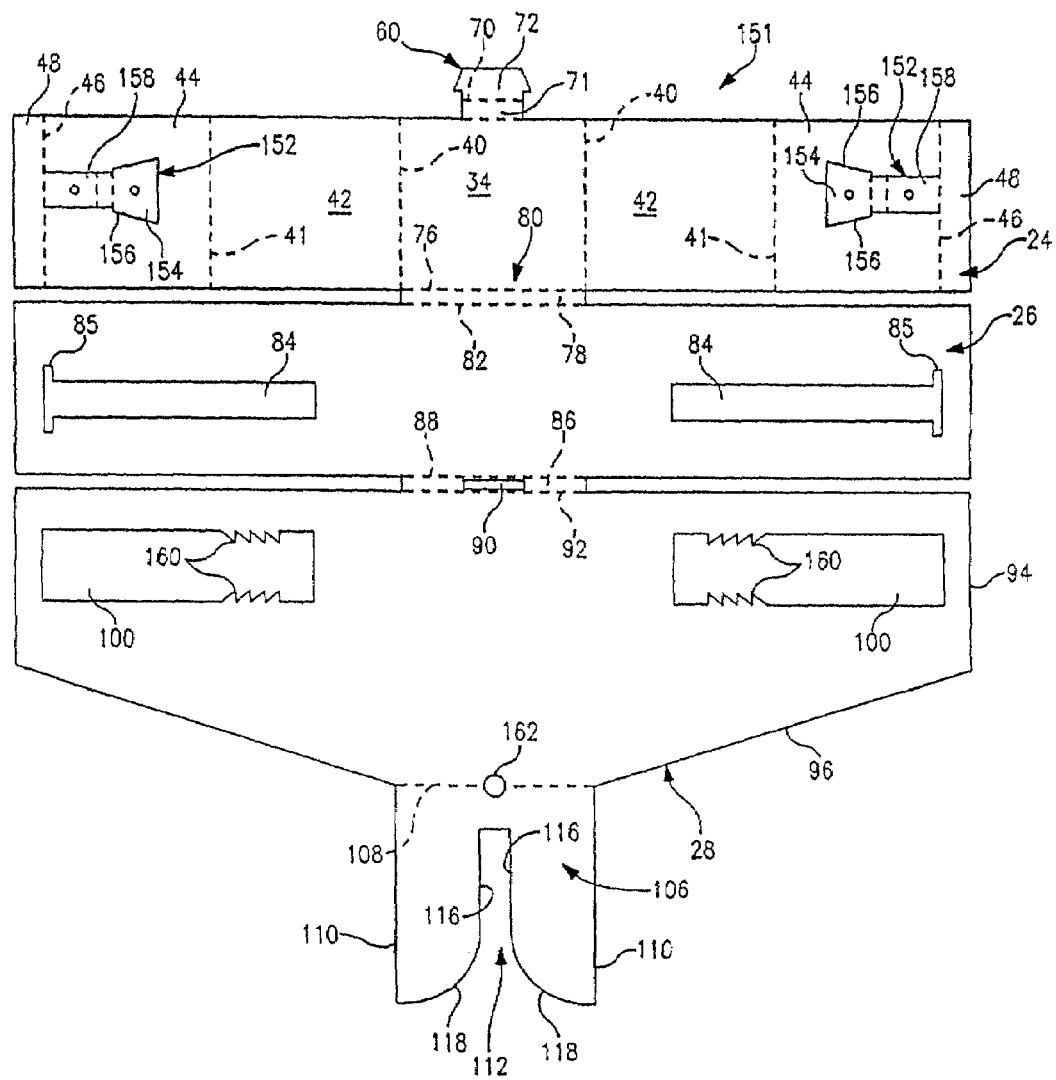
FIG. 15 is a top plan view of a blank for forming a cervical immobilization device in a third embodiment of the invention.

FIG. 15 illustrates a blank 151 for forming the cervical immobilization device 150 and includes panels 24, 26, 28, and 106 that are substantially the same as the previous embodiment. The embodiment of FIG. 15 differs primarily from the embodiment of FIG. 1 in that the outer panels 44 include a cut portion 50 to form tabs 152 having a substantially trapezoidal-shaped head 154. As shown, the head 154 includes angled sides 156 which converge toward the neck portion 158.

The slots 100 in panel 26 include a plurality of teeth 160 extending inward from each side of the slot. The teeth 160 are dimensioned to interlock with the angled sides 156 of the tabs 152. The teeth as shown have a first face 161 angled in the direction of the outer edges and a second face 163 extending substantially perpendicular to the side edge of the slot 100. Alternatively, a single slot can be formed to accommodate the tabs 152. A hole 162 is punched along the fold line 108 for the reversible actuating device 164.

Figure 16:
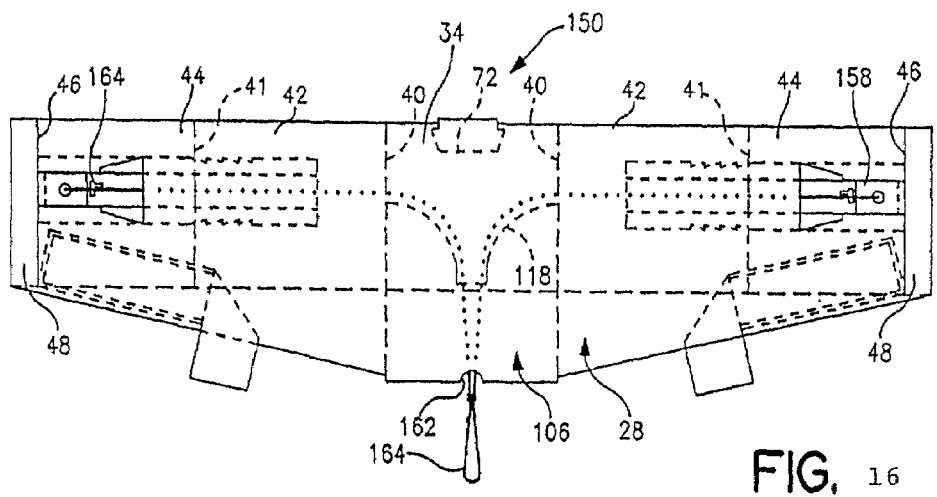
FIG. 16 is a top plan view of the cervical immobilization device formed from the blank of FIG. 15.

FIG. 16 is a top view of the assembled cervical immobilization device 150. The reversible actuating device 164 is a flexible member such as a string or cord attached to each coupling tab 152 and passes through the hole 162 around each of the convex surfaces 118. The reversible actuating device 164 is pulled outward from the cervical immobilization device 150. The pulling of the reversible actuating device 164 also pulls the tabs 152 and the outer ends of the arms 16 toward the center panel 34 to the upright folded position.

Figure 17:
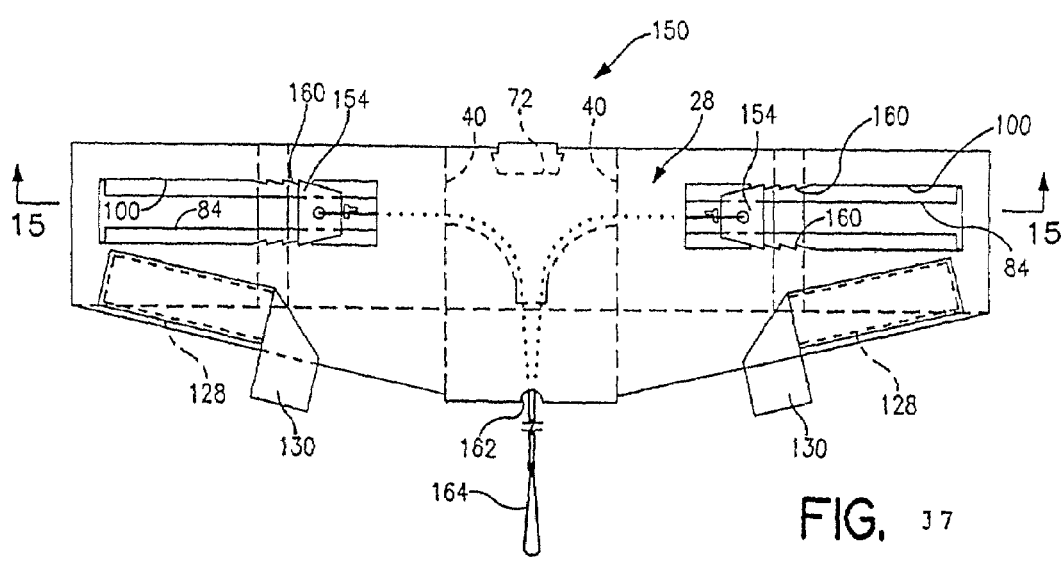
FIG. 17 is a bottom view of the cervical immobilization device of FIG. 16 showing the head engaging arms in the folded position.

FIG. 17 illustrates the position of the reversible actuating device 164 after it is pulled. The reversible actuating device 164 also pulls the tabs 152 along the slot 100 where the sides 156 engage the teeth 160 in a ratcheting motion. The edges 156 engage the teeth 160 to lock the tabs 152 in a fixed position.

Figure 18:
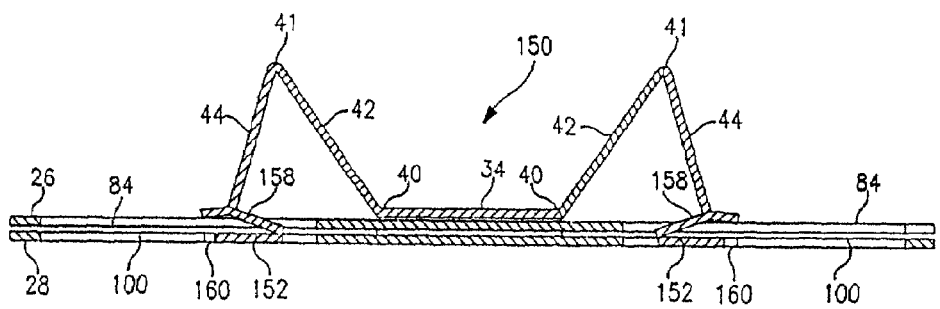
FIG. 18 is a cross-sectional view showing the head engaging arms in the folded position.

FIG. 18 illustrates the position of the teeth 160 in relation to the tabs 152. The teeth 160 allow the tabs 152 to slide or ratchet in the direction of the center panel 34 and prevent the tabs 152 from sliding back to the original position. In desirable embodiments, the tabs 152 can be manually released by the user and the inner panel 42 and outer panel 44 returned to their inoperable or flat positions. The action of manually releasing and sliding the panels also returns the reversible actuating device 164 to its first or inoperable position.

Figure 19:
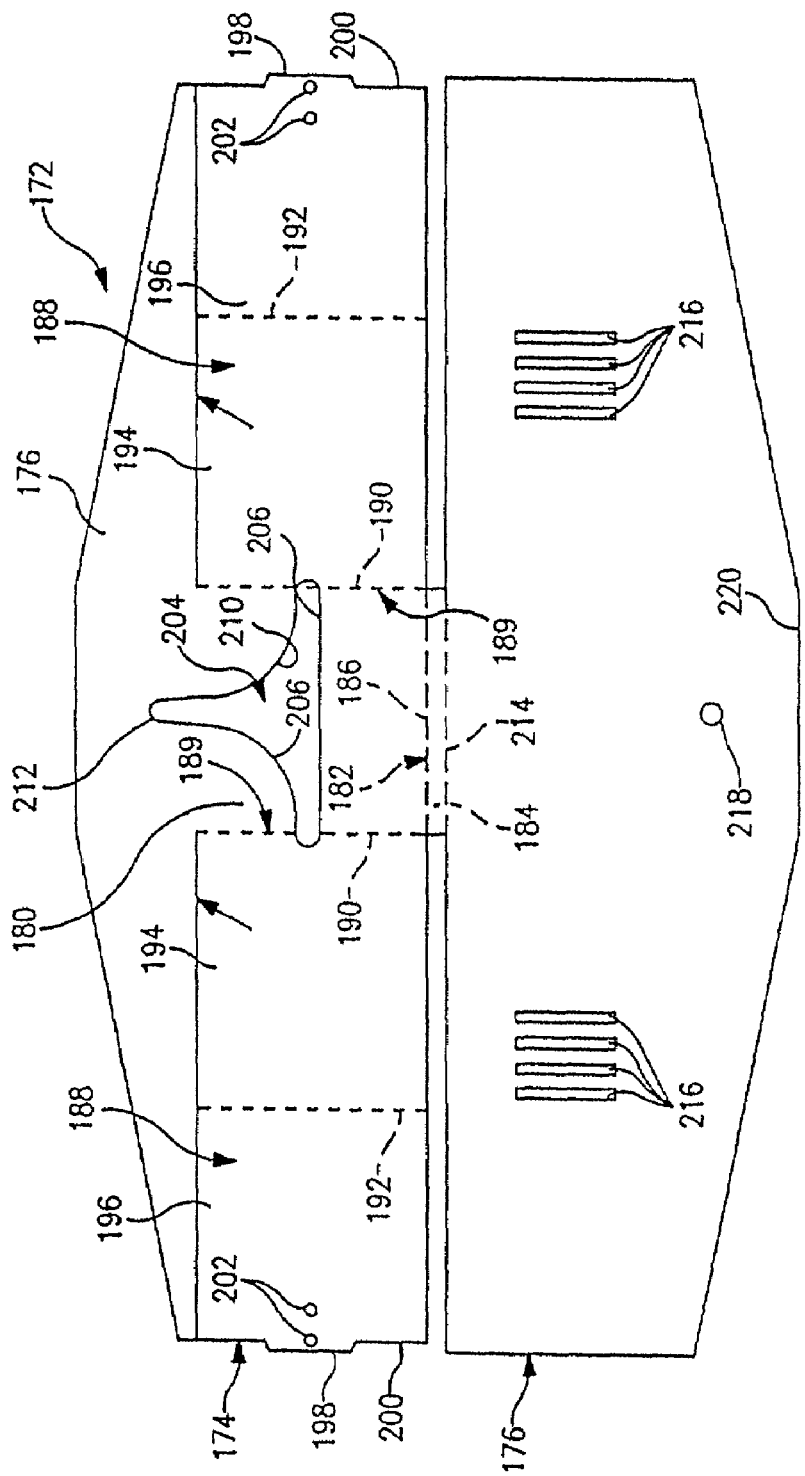
FIG. 19 is a top plan view of a blank for forming a cervical immobilization device in a further embodiment of the invention.

FIGS. 19 through 21 illustrate a further embodiment of the invention. This embodiment is similar to the previous embodiments, except that the cervical immobilization device 170 is formed from two layers of material superimposed on one another.

FIG. 19 illustrates a blank 172 that is used to form the cervical immobilization device 170, as illustrated in FIG. 21. The blank 172 includes a first panel 174 and a second panel 176. The first panel 174 includes an outer portion 178 extending the length of the first panel in the longitudinal direction and is integrally formed with a center panel 180. The center panel 180 has a longitudinal edge 182 coupled to a coupling panel 184 by a fold line 186. The center panel 180 also has transverse side edges 189 coupled to identical flaps 188 by fold lines 190. Each of the flaps 188 has a longitudinal dimension extending to the edge of the outer portion 178. The flaps 188 include a center fold line 192 to define an inner panel 194 and an outer panel 196. A coupling tab 198 extends from the edge 200 of the outer panel 196. A pair of apertures 202 are formed in the outer panel 196 adjacent the coupling tab 198.

The center panel 180 includes a center aperture 204 having a generally triangular shape. The aperture 204 has a first edge 206 extending in the longitudinal direction of the first panel 174 and has a length slightly greater than the width of the center panel 180 so that the aperture 204 extends into each inner panel 194. A second edge 208 and a third edge 210 extend from the first edge 206 and converge to an apex 212. The second and third edges have a generally convex shape as shown in FIG. 19. As shown, each of the side edges joins an adjacent side edge at a generally curved intersection.

The coupling panel 184 is coupled to the second panel 176 by a fold line 214. The second panel 176 has an overall dimension and shape substantially the same as the first panel 174. As shown in FIG. 19, a plurality of spaced-apart slots 216 is formed in the second panel extending in a generally transverse direction with respect to the longitudinal dimension of the second panel 176. The slots 116 have a length and width sufficient for receiving the coupling tab 198. A central aperture 218 is provided in the second panel 176 proximate the outer longitudinal edge 220 of the second panel 176.

FIG. 20 also illustrates the cervical immobilization device 170. The cervical immobilization device 170 is formed by folding the first panel 176 along fold lines 186 and 214 so that the first and second panels are superimposed on one another. The outer portion 178 of the first panel 174 and the center panel 180 are preferably attached to the second panel 176 by a suitable adhesive or fastening device. A reversible actuating device 222 is coupled to the outer ends of the flaps 188 adjacent to the coupling tabs 198. The reversible actuating device 222 extends between the first and second panels toward the center aperture 204 and is guided along the convex edges 208 and 210 to the aperture 218. The reversible actuating device 222 extends through the aperture 218 and extends beyond the edge 220 of the panels 174 and 176 a sufficient distance to be gripped by a user.

The reversible actuating device 222 of this embodiment can be a flexible cord or a flexible rod having each end attached to a respective end of the first panel. A suitable clamping device 224 is provided on the reversible actuating device 222 to limit the movement of the reversible actuating device through the aperture 218. The clamping device 224 can be a spring-based clamp capable of gripping the reversible actuating device and preventing the reversible actuating device from retracting in the cervical immobilization device 170. Other embodiments of the clamping device 224 can include a post to insert into a hole in the reversible actuating device, a ratchet and pawl mechanism, a screw, a button-like device, and/or an equivalent locking means.

A top panel 226 is positioned over the center panel 180 to cover the aperture 204. Desirably, the top panel 226 is dimensioned to cover the center panel 180 completely and is attached thereto by a suitable adhesive or other fastening device. Generally, the top panel 226 is a flexible cushioning foam for supporting a patient's head, although other materials can be used.

The cervical immobilization device 170 is used in a similar manner to the previous embodiments. As in the previous embodiments, the cervical immobilization device 170 is attached to a rigid backboard by adhesive strips 228 on the bottom side of the second panel 176. A patient's head is placed on the top panel 226 with the reversible actuating device 222 extending away from the patient's body. The reversible actuating device 222 is pulled away from the center panel 180 which draws the outer edges of the flaps 188 inward toward the center panel.

FIG. 21 illustrates the cervical immobilization device 170 with the outer edges of the flaps 188 pulled toward the center panel. The flaps 188 fold along the fold lines 190 and 192 to an upright position.

The reversible actuating device 222 pulls the outer edges of the flaps 188 to an upright position in a symmetrical fashion to avoid or reduce movement of the patient's head during the use of the device. The coupling tabs 198 slide along the second panel 176 and are received in one of the slots 216 to lock the outer panel 196 in a fixed position. The different slots 216 allow selective adjustment of the position of the coupling tabs 198 to accommodate different patients. Although four slots are shown for each of the coupling tabs 198, additional or fewer slots can be used as needed to accommodate different sizes of patients.

The reversible actuating device 222 is pulled to a position where the inner panels 194 contact the patient's head and conform to the shape of the patient's head and the coupling tab 198 is positioned in the appropriate slot 216. The suitable strap or tape is then placed across the forehead of the patient and attached to the cervical immobilization device 170 to secure the patient's head in a fixed position. The clamping device 224 can be slid along the reversible actuating device 222 until it engages the edge of the cervical immobilization device 170 to prevent the reversible actuating device 222 from retracting into the cervical immobilization device and allowing the flaps 188 to unfold or return to their original position.

Figure 22:
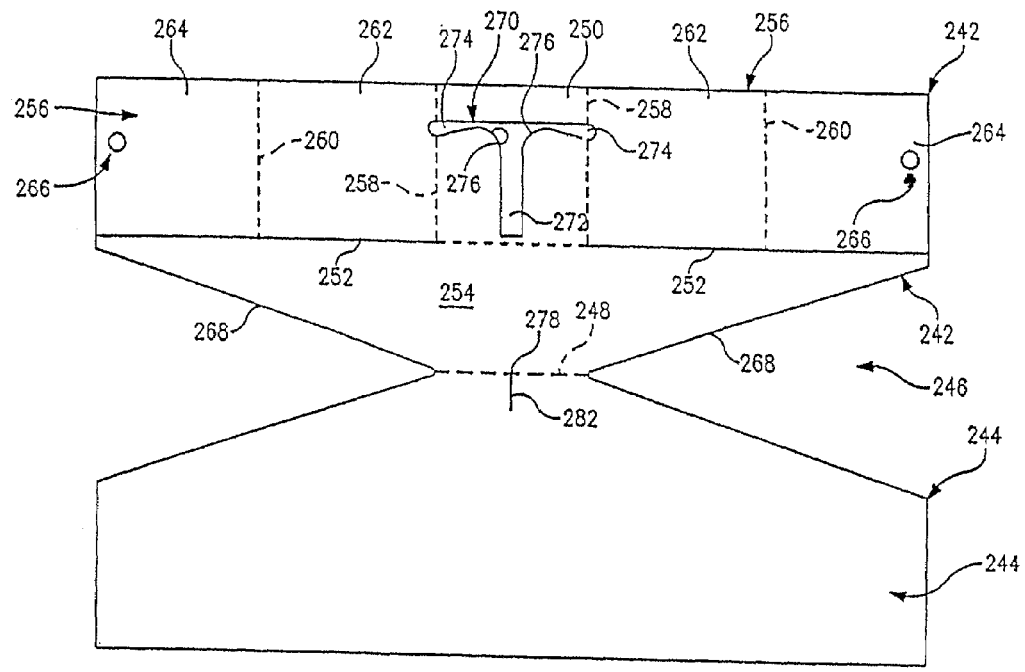
FIG. 22 is a top plan view of a blank in a further embodiment of the invention.
Figure 23:
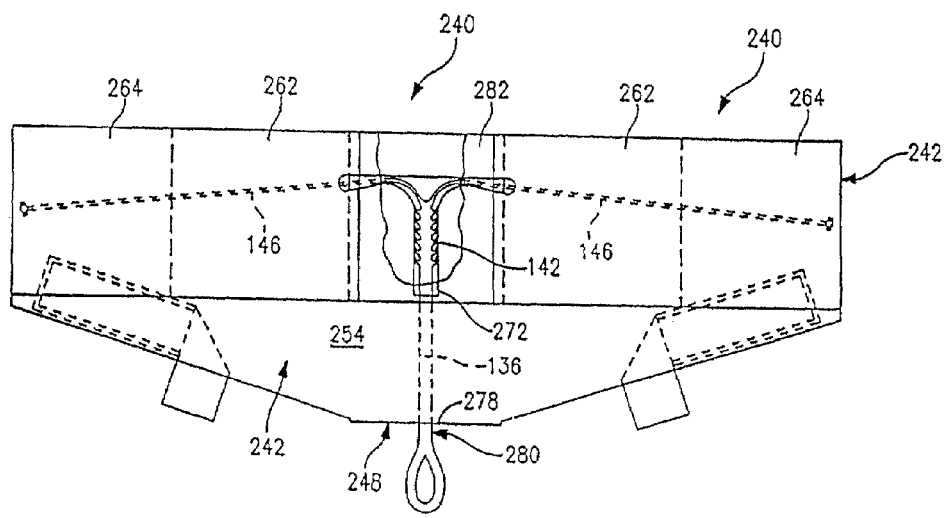
FIG. 23 is a top plan view of the cervical immobilization device made from the blank of FIG. 22.

FIGS. 22 and 23 illustrate a further embodiment of the cervical immobilization device 240. The cervical immobilization device 240 is formed from two superimposed panels 242 and 244. The cervical immobilization device 240 can be formed from separate panels that are bonded together. In the illustrated embodiment, the device 240 is made from a folded blank 246 of cardboard or other material. The blank 240 includes the first panel 242 and the second panel 244 coupled together along a fold line 248. The first panel 242 and the second panel 244 are substantially the same shape and size.

The first panel 242 includes a center panel 250 and cut lines 252 to form a top portion 254 and arms 256. Each arm 256 is coupled to the side edges of the center panel 250 by a fold line 258. The arms 256 include an intermediate fold line 260 to define an inner panel 262 and outer panel 264. An aperture 266 is formed in each of the outer panels 264 adjacent to the outermost edges.

The top portion 254 of panel 242 has a longitudinal dimension equal to the combined longitudinal dimension of the arms 256 and the center panel 250. The top portion has a generally truncated triangular shape with side edges 268 converging toward the fold line 248. A slit 278 is formed along the fold line 248.

The center panel 250 includes a generally T-shaped aperture 270 having a base portion 272 extending in the direction of the fold line 248 and a pair of arm portions 274. As shown in FIG. 22, the arm portions 274 have a curved portion 276. The arm portions 274 have a length to extend a slight distance past the fold lines 258 into the inner panels 262.

The cervical immobilization device 240 is formed by folding the blank 246 along the fold line 248 and attaching the panels 242 and 244 together. Generally, the top portion 254 at the center fold is attached to the second panel 244 by a suitable adhesive. The arms 256, as in the previous embodiments, are movable with respect to the second panel 244.

A reversible actuating device 280 is attached to each end of the arms by inserting the free end through the apertures 266. The reversible actuating device 280 is substantially the same as in the previous embodiments, so identical elements are identified by the same reference numbers. The end of the reversible actuating device is fed through a transverse slit 282 in the second panel 244 and positioned in the longitudinal slit as shown in FIG. 23. The flexible legs of the reversible actuating device extend around the curved portions 276 of the aperture 270, which serve as a guide for the flexible legs. A flexible cushion or pad 284 is generally attached to the center panel to cover the aperture in the center panel.

The cervical immobilization device 240 is used in a similar manner as the previous embodiments. The reversible actuating device 280 is pulled by the user so that the arms 256 are moved to a folded upright position as in the previous embodiments. The teeth of the reversible actuating device 280 are pulled through the slit 282 to engage the walls of the slit 278 and lock the arms in the folded position.

FIGS. 24 through 26 illustrate the preferred embodiment of a reversible actuating device 334. The reversible actuating device 334 includes a body portion 136 having an infinite or finite plurality of sizing positions. In this embodiment the sizing positions are a finite number of ratchet teeth 338 on one surface of the body portion 136. Embodiments having an infinite number of sizing positions include a smooth reversible actuating device that is gripped by a friction means such as a screw, clamp, or similar friction-engaging means. A reversible actuating device having an infinite number of sizing positions can also be constructed with hook-and-loop fabric, releasable adhesives, or similar adhering means.

A gripping end 340 is provided on the reversible actuating device 334 in the form of a ring-shaped or D-shaped loop. The reversible actuating device 334 has attachment means at the end of one or more flexible legs 146. The attachment means engages the cervical immobilizing member. The attachment means of this embodiment is a hook-shaped member 348. The hook-shaped member 348 of this embodiment has two hooks, but a single hook, conical-shaped tip, ball, or similar attachment means can be used.

FIGS. 27 and 28 illustrate an embodiment of a rigid member 301. In this embodiment the rigid member 301 has a flat base 311 of any geometrical shape that supports at least one engagement means. The engagement means of this preferred embodiment includes a pawl 322 mounted on an extension 321 wherein the width of the pawl 322 is broader than the width of the extension 321. This geometrical arrangement is of suitable dimensions to permit this embodiment of the rigid member 301 to be assembled into a slot in the cervical immobilization device as explained below.

The engagement means or pawl 322 with or without an extension 321 can be any geometrical shape which engages the ratchet teeth 338 of the reversible actuating device 334. This embodiment illustrates a pawl 332, but similar stop means can be used for engaging ratchet teeth or other means on a reversible actuating device such as protrusions, holes, ridges, or the like.

FIG. 29 illustrates an enlargement of the rigid member 301 engaging the reversible actuating device 334. The embodiment of the rigid member 301 of this figure has a single straight-edged pawl 322 of a geometrical configuration to engage the complementary ratchet teeth 338.

Figure 30:
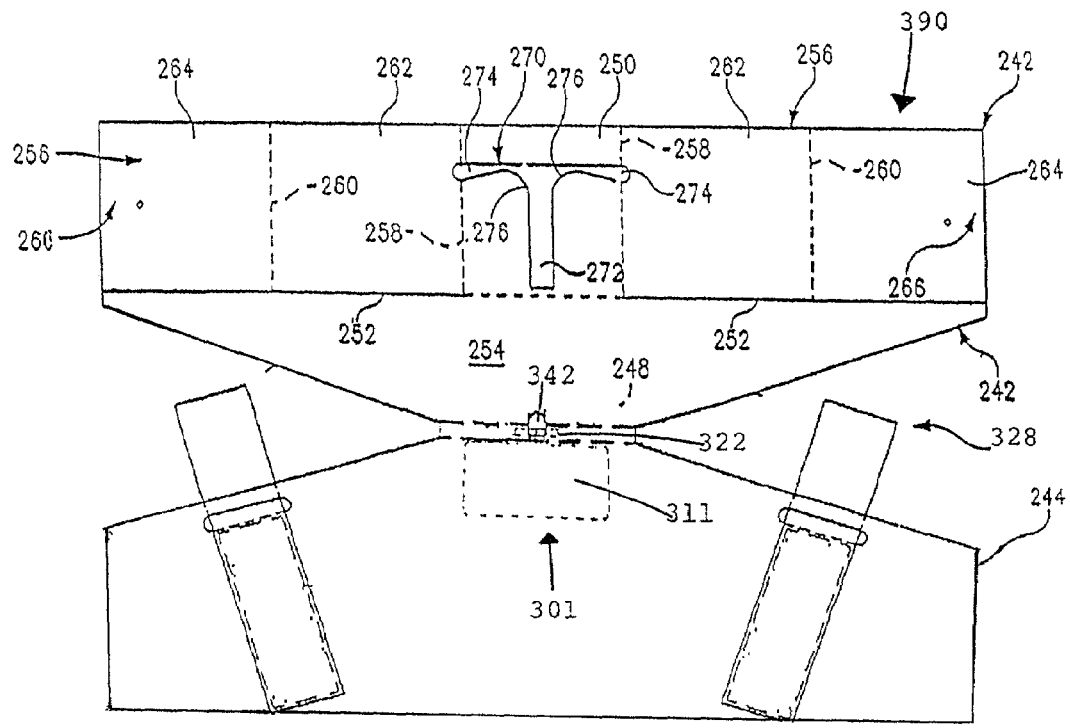
FIG. 30 is a top plan view of the cervical immobilization device of the preferred embodiment of the invention.
Figure 31:
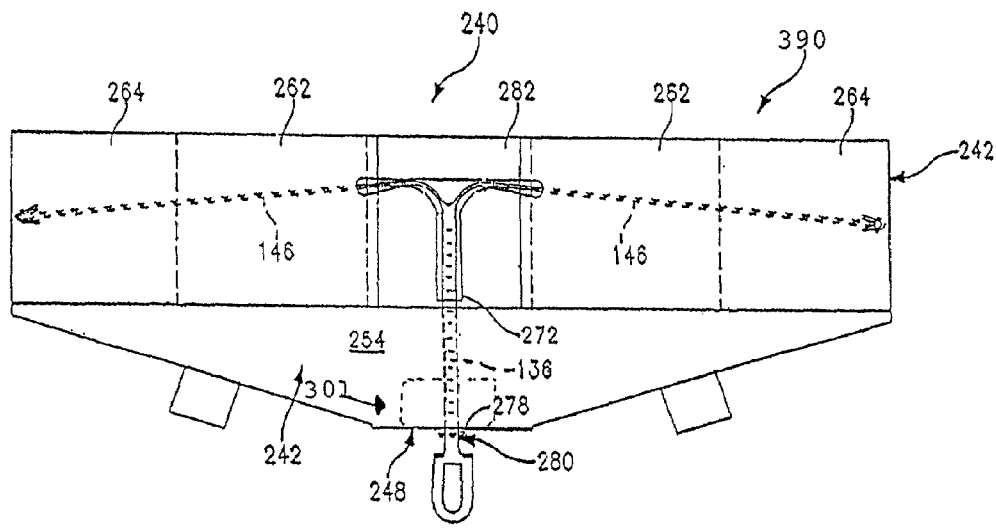
FIG. 31 is a top plan view of the cervical immobilization device of the embodiment of FIG. 30.

FIGS. 30 and 31 illustrate the preferred embodiment of the cervical immobilization device 390. The rigid member 301 is illustrated after the pawl 322 is inserted through slot 342, turned, and positioned under the second panel 244. This embodiment has the benefit of simple and expedient assembly without the need for adhesive to hold the rigid member 301 in place. The use of a rigid member 301 in lieu of the edges of slot 342 to engage a reversible actuating device permits the cervical immobilization device 390 to be made of inexpensive cardboard and provide a significant number of multiple uses. This embodiment also illustrates the preferred arrangement for optional adhesive strips 328.

FIG. 32 illustrates an alternative reversible actuating device 434. The gripping end 340 is used to pull the reversible actuating device 434 and the flexible legs 146. A body portion 436 has a finite plurality of sizing positions or holes 438. A single hook 448 is at the end of each flexible leg 146 to engage the cervical immobilizing member. Each leg includes a pushing means or protrusion 450 such that the arms 16 can be returned to a flat position by pushing the reversible actuating device 434 back into a cervical immobilization device. The pushing means can alternatively be a notch, hook, barb, adhesive, attachment device such as a screw, hook and loop fabric, or similar means.

FIGS. 33 and 34 illustrate an alternative embodiment of a rigid member 302 having a post 420. The rigid member 302 has a base 410 of any geometrical shape that supports at least one engagement means or in this embodiment a post 420. The post 420 can be any geometrical shape which engages the holes 438 of the reversible actuating device 434.

FIG. 35 illustrates an enlargement of the rigid member 302 engaging the reversible actuating device 434. The embodiment of the rigid member 302 of this figure has a single post not mounted on an extension from the base.

An alternative embodiment of the cervical immobilization device (not shown) can use a rack and pinion and/or tooth and gear configuration to guide the two-directional movement of a reversible actuating device. Such a structure requires a rigid and resilient construction. Such a structure can be more expensive, but the movement of the parts is precise and smooth. Suitable locks or lock means can be use with these embodiments of the reversible actuating device.

Several embodiments have been chosen to illustrate the invention. It will be appreciated by those skilled in the art that various other modifications and embodiments can be constructed without departing from the various features of the invention. For example, the reversible actuating device in each of the illustrated embodiments is a flexible member that is pulled away from the device to pull the outer ends of the support arms of the device toward the patient's head to a locked position. In further embodiments, the reversible actuating device can be an assembly of flexible or rigid components or levers that can be either pushed or pulled to draw the arms from the flat position to the upright position for engaging the patient's head. In a further embodiment, the reversible actuating device can include a pair of rigid levers extending from the outer ends of the arms and coupled together by a pivot mechanism at the center of the device. An arm or lever can be attached to the pivot device that can be pulled or pushed causing a scissor-like action of the rigid members to pull the outer ends of the flaps toward the center of the device. In a similar manner, the locking device can be other arrangements for fixing the position of the arms in the folded position during use.

The invention is a cervical immobilization device that collapses into a flat condition for storage and smoothly and folds into an operable condition wherein cervical immobilization members become upright and engage the sides of a patient's head. Desirable embodiments of the invention can be economically manufactured from inexpensive materials, rendering the device disposable if contaminated by a patient's body fluids. The device can be attached to a rigid backboard. Desirable embodiments of the invention have an reversible actuating device that enables head-engaging arms to engage simultaneously and symmetrically a patient's head when folded into an operating position so as to eliminate or reduce movement of the patient's head. The preferred reversible actuating device can be operated by the user with one hand to engage symmetrically both sides of the patient's head to prevent twisting of the head and to support the patient's head during transport.

What is claimed is:

1. A cervical immobilization device, comprising:
a base having two opposite ends, a front edge, and a rear edge;
a cervical immobilizing member coupled to said base and including (i) a center portion and (ii) at least two opposite movable arms with each of said movable arms being foldable between a first position and a second folded position for engaging a patient's head, each of said movable arms having:
a pivotal coupling between an inner edge of each of said movable arms and said center portion and
an outer edge facing outward toward a respective one of said opposite ends of said base; and
a reversible actuating device, said reversible actuating device is a flexible member, said flexible member has at least two flexible leg members, said reversible actuating device slides said outer edge of each of said movable arms to said second folded position.

2. The cervical immobilization device of claim 1, wherein said reversible actuating device both folds and unfolds said movable arms.

3. The cervical immobilization device of claim 1, wherein said reversible actuating device includes more than one piece.

4. The cervical immobilization device of claim 1, wherein said flexible leg members include a pushing means.

5. The cervical immobilization device of claim 1, wherein said reversible actuating device includes a lock.

6. The cervical immobilization device of claim 5, wherein said lock is a post and hole mechanism.

7. The cervical immobilization device of claim 1, further comprising a guide member for guiding said reversible actuating device.

8. The cervical immobilization device of claim 7, wherein said guide member includes an elongated slot through which said reversible actuating device passes, whereby pulling said reversible actuating device through said slot pulls said movable arms toward said center portion to said second folded position.

9. A cervical immobilization device, comprising:
a base having two opposite ends, a front edge, and a rear edge;
a cervical immobilizing member coupled to said base and including (i) a center portion and (ii) at least two opposite movable arms with each of said movable arms being foldable between a first position and a second folded position for engaging a patient's head, each of said movable arms having:
a pivotal coupling between an inner edge of each of said movable arms and said center portion and
an outer edge facing outward toward a respective one of said opposite ends of said base; and
a reversible actuating device, said reversible actuating device includes a rod attached to a first end of at least two flexible members, a second end of said flexible members is fixed to one of said movable arms, said rod rotates to wind said flexible members, said reversible actuating device slides said outer edge of each of said movable arms to said second folded position.

10. The cervical immobilization device of claim 9, wherein said reversible actuating device both folds and unfolds said movable arms.

11. The cervical immobilization device of claim 9, wherein said reversible actuating device includes more than one piece.

12. The cervical immobilization device of claim 9, wherein said flexible members are stiff and include a pushing means.

13. The cervical immobilization device of claim 9, wherein said reversible actuating device includes a lock.

14. The cervical immobilization device of claim 9, wherein said lock is a post and hole mechanism.

15. The cervical immobilization device of claim 9, further comprising a guide member for guiding said reversible actuating device.

16. The cervical immobilization device of claim 15, wherein said guide member includes an elongated slot through which said reversible actuating device passes, whereby pulling said reversible actuating device through said slot pulls said movable arms toward said center portion to said second folded position.

* * * * *